United States Patent
Yoshii et al.

(10) Patent No.: US 7,919,596 B2
(45) Date of Patent: Apr. 5, 2011

(54) METHOD OF ARRANGING FERRITIN AND METHOD OF ARRANGING INORGANIC PARTICLES

(75) Inventors: Shigeo Yoshii, Osaka (JP); Kazuaki Nishio, Osaka (JP); Shinya Kumagai, Kyoto (JP); Ichiro Yamashita, Nara (JP)

(73) Assignee: Panasonic Corporation, Osaka (JP)

( * ) Notice: Subject to any disclaimer, the term of this patent is extended or adjusted under 35 U.S.C. 154(b) by 182 days.

(21) Appl. No.: 12/320,556

(22) Filed: Jan. 29, 2009

(65) Prior Publication Data

US 2009/0187010 A1 Jul. 23, 2009

Related U.S. Application Data

(63) Continuation of application No. PCT/JP2008/001135, filed on May 1, 2008.

(30) Foreign Application Priority Data

Jun. 15, 2007 (JP) ................................ 2007-159123

(51) Int. Cl.
*C07K 14/00* (2006.01)
*H01L 21/00* (2006.01)
*H01L 21/314* (2006.01)
*H01L 21/471* (2006.01)

(52) U.S. Cl. ............. 530/400; 438/1; 438/778; 435/7.1; 378/34

(58) Field of Classification Search ........................ None
See application file for complete search history.

(56) References Cited

U.S. PATENT DOCUMENTS

| 2004/0142164 A1 | 7/2004 | Yamashita |
| 2006/0121628 A1 | 6/2006 | Yamashita |

FOREIGN PATENT DOCUMENTS

| JP | 2003-033191 | 2/2003 |
| JP | 2006-187844 | 7/2006 |
| JP | 2006-187845 | 7/2006 |
| WO | WO 03/040025 A1 | 5/2003 |
| WO | WO 2006/064640 A1 | 6/2006 |

OTHER PUBLICATIONS

Yuan, et al. 1998 Proteins 30: 136-143.*
Lee, et al. 1995 The EMBO Journal 14(20): 5006-5015.*
Shinya Kumagai, et al., "Electrostatic placement of single ferritin molecules", Applied Physics Letters, 2006, vol. 88, p. 153103, American Institute of Physics.
Takuro Matsui, et al., "Realizing a Two-Dimensional Ordered Array of Ferritin Molecules Directly on a Solid Surface Utilizing Carbonaceous Material Affinity Peptides", Langmuir, 2007, vol. 23, pp. 1615-1618, American Chemical Society.
David Lawson., et al., "Solving the structure of human H ferritin by genetically engineering intermolecular crystal contacts", Nature, Feb. 7, 1991, vol. 349, pp. 541-544, Nature Publishing Group.
Kuniaki Nagayama., et al., "Fabrication and Control of Two-Dimensional Crystalline Arrays of Protein Molecules", Jpn. J. Appl. Phys., Jul. 1995, Vol. 34 Part 1, No. 7B, pp. 3947-3954.
Shinya Kumagai, et al., "Electrostatic Placement of Nanodots onto Silicon Substrate Using Ferritin Protein Supramolecules with Control of Electrostatic Interaction in Solution", Japanese Journal of Applied Physics, 2006, vol. 45 No. 10B, pp. 8311-8316, The Japan Society of Applied Physics.

* cited by examiner

*Primary Examiner* — David J Steadman
*Assistant Examiner* — Marsha M Tsay
(74) *Attorney, Agent, or Firm* — McDermott Will & Emery LLP

(57) ABSTRACT

To provide a method of arranging ferritin by which a high rate of the number of the molecular film spots on which sole ferritin molecule was arranged in effect, with respect to total number of the molecular film spots provided for arranging ferritin (sole arrangement rate) is achieved is objected to. Specifically, in Fer8 ferritin having a sequence excluding 7 amino acids of from the second to the eighth, from an amino acid sequence (Fer0 sequence) translated from a naturally occurring DNA sequence, lysine at position 91 is substituted with glutamic acid.

12 Claims, 13 Drawing Sheets

METHOD OF ARRANGING FERRITIN AND METHOD OF ARRANGING INORGANIC PARTICLES

RELATED APPLICATIONS

This application is a continuation of International Application No. PCT/JP2008/001135, filed on May 1, 2008, which in turn claims the benefit of Japanese Application No. 2007-159123, filed on Jun. 15, 2007, the disclosures of which Applications are incorporated by reference herein.

BACKGROUND OF THE INVENTION

1. Field of the Invention

The present invention relates to a method of arranging minute particles on a substrate through utilization of a protein.

2. Related Art

Ferritin is a spherical protein that includes a metal compound therein which is typified by iron oxide. When any metal compound is not included therein but has a hollow space inside, ferritin is referred to as "apoferritin".

Japanese Unexamined Patent Publication No. 2006-187844 (Patent Document 1) and Japanese Unexamined Patent Publication No. 2006-187845 (Patent Document 2) disclose as the first prior art for arranging ferritin on a substrate, to arrange a plural number of molecules of ferritin on an aminosilane molecule-modified film by forming the aminosilane molecule-modified film on a part of the substrate surface, and bringing the same into contact with a ferritin solution.

Kumagai et al., Jpn. J. Appl. Phys. 45 (2006) 8311 (Nonpatent Document 1) and Kumagai et al., Appl. Phys. Lett. 88 (2006) 153103 (Nonpatent Document 2) disclose as the second prior art, to arrange one, (i.e., single) ferritin molecule on each molecular film spot by forming a minute molecular film spot constituted with aminosilane on a part of a substrate surface, and then bringing this substrate into contact with a ferritin solution. According to the Nonpatent Documents 1 and 2, the position where single ferritin molecule is arranged on a substrate can be freely determined.

Pamphlet of International Publication No. 2003/040025 (Patent Document 3) discloses as the third prior art, a process for regularly arraying ferritin on a substrate through partially substituting an amino acid on the external side surface of ferritin. According to Patent Document 3, an amino acid at a certain position on the external side surface is substituted with a positively or negatively charged amino acid.

Japanese Unexamined Patent Publication No. 2003-033191 (Patent Document 4) discloses as the fourth prior art, to permit inclusion of a noble metal typified by gold into apoferritin through partially substituting the amino acid on the inner side surface of apoferritin.

SUMMARY OF THE INVENTION

Patent Documents 1, 2, and 4 do not disclose any technique for arranging sole ferritin through positioning on a substrate.

To the contrary, according to the techniques disclosed in Nonpatent Documents 1 and 2, sole ferritin can be arranged on a substrate through positioning. Further, according to the technique disclosed in Patent Document 3, the amino acid on the external side surface of ferritin is substituted with a positively or negatively charged amino acid.

Therefore, when Patent Document 3 is combined with Nonpatent Documents 1 and 2, the technique as follows is derived. That is, minute molecular film spots constituted with positively charged aminosilane are formed on a part of the substrate surface, and this substrate is then brought into contact with ferritin having substitution of an amino acid on the external side surface with a negatively charged amino acid. Thus, single ferritin molecule can be arranged on each molecular film spot.

However, according to investigations by the present inventors, it was revealed that the following two problems are caused when sole ferritin molecule is arranged through positioning on a substrate.

The first problem lies with low reproducibility of arranging ferritin through positioning. Provided that the rate of molecular film spots on which sole ferritin molecule is arranged in effect, with respect to total number of the molecular film spots provided for arranging ferritin is referred to as "sole arrangement rate", the sole arrangement rate according to the prior arts is just approximately 60 to 70%.

The second problem is that minute spots having a diameter of less than 30 nm must be formed as the molecular film spot for arranging ferritin. Formation of spots no larger than 30 nm is difficult according to common photolithography. Thus, use of an apparatus that is expensive and inferior in productivity typified by an electronic beam exposure apparatus is required.

Theoretically, as shown in FIG. 12 (a), one molecule of ferritin is arranged on one molecular film spot when diameter A of the molecular film spot is identical with external diameter B of ferritin. However, the external diameter of ferritin is about 12 to 13 nm, and thus to form a molecular film spot having such a diameter is difficult since formation of too small molecular film spot is obliged. In particular, to form the molecular film spot having such a diameter by photolithography would be impossible.

Therefore, the diameter A of the molecular film spot is determined to be greater than the external diameter B of ferritin in effect. However, as shown in FIG. 12 (b), arrangement of two or more molecules of ferritin on one molecular film spot is inevitable according to such a process.

In addition, as a result of ceaseless researches by the present inventors, the following fact was also found. That is, it is assumed that substitution of the amino acid being present on the external side surface of ferritin with a negatively charged amino acid, as negative as possible, tends to be desired, in light of the electrical attraction to the molecular film spot, and also in light of the repulsive force between ferritin molecules.

However, as a result of experiments carried out in effect, it was found the such a tendency is absent, and also found that the sole arrangement rate is completely different depending on the substituted position even though the amino acids are substituted in an identical number, as would be also understood from Examples and Comparative Examples described herein later.

The method of arranging ferritin according to the present invention for solving the foregoing problems is a method of arranging ferritin on a substrate provided with a plurality of molecular film spots, in which the ferritin is modified ferritin constituted with a protein subunit having an amino acid sequence set out in SEQ ID NO: 1;

the molecular film spot has an amino group on the surface thereof;

the area of one molecular film spot is equal to or less than 2,100 nm$^2$; and the method includes an arrangement step of arranging one molecule of the ferritin on each molecular film spot by bringing a solution containing the ferritin into contact with the substrate.

The method of arranging inorganic particles according to the present invention for solving the foregoing problems is a method of arranging inorganic particles on a substrate, the method including:

an arrangement step of arranging one molecule of the ferritin on one molecular film spot by bringing a solution containing ferritin into contact with the substrate provided with a plurality of molecular film spots; and a decomposition step of decomposing the ferritin by heating the substrate, in which the ferritin is modified ferritin constituted with a protein subunit having an amino acid sequence set out in SEQ ID NO: 1;

the molecular film spot has an amino group on the surface thereof; and the area of one molecular film spot is equal to or less than 2,100 nm$^2$.

The modified ferritin preferably includes an iron oxide particle therein.

The molecular film spot is preferably constituted with an aminosilane molecular film.

It is preferred that the substrate be a silicon substrate, and be provided with a silicon oxide film in the region except for the molecular film on the substrate surface.

The area of one molecular film spot is preferably equal to or greater than 380 nm$^2$.

It is preferred that the method further includes prior to the arrangement step a molecular film spot formation step of forming the molecular film spot by photolithography.

The foregoing objects, other objects, features and advantages of the present invention will be apparent from the detailed description of the following preferred embodiments with reference to the accompanying drawings.

ADVANTAGES OF THE INVENTION

According to the present invention, a method of arranging ferritin with a high sole arrangement rate, and a method of arranging inorganic particles are provided.

DETAILED DESCRIPTION OF THE INVENTION

Figure 1:
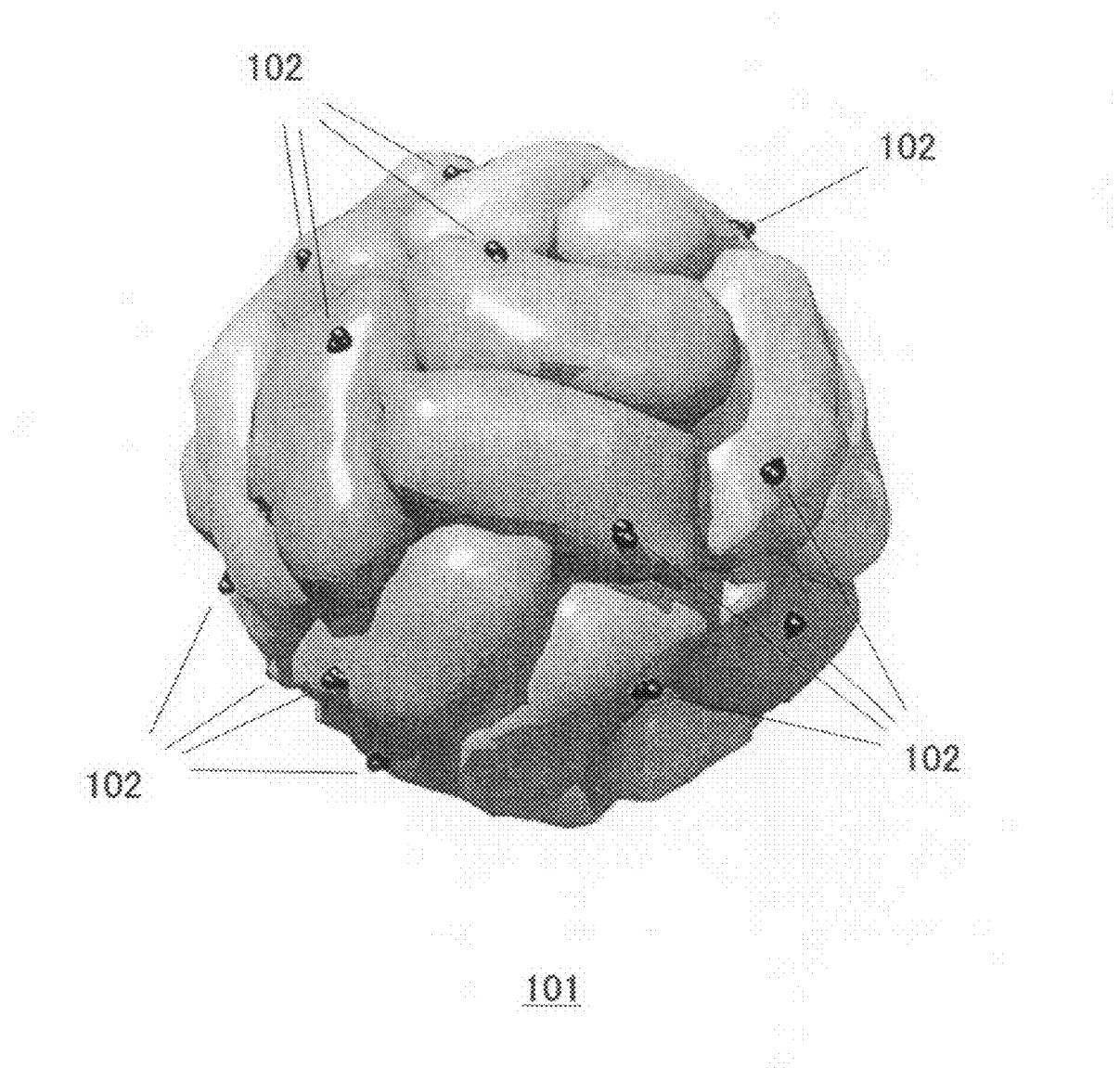
FIG. 1 shows a schematic view illustrating modified ferritin apoFer8-98glu.

The modified ferritin used in the present invention is constituted with 24 protein subunits having an amino acid sequence set out in SEQ ID NO: 1. A schematic view of this modified ferritin 101 is shown in FIG. 1. SEQ ID NO: 1 is constructed on the basis of the amino acid sequence that constitutes L chain of ferritin derived from horse, but glutamic acid at position 91 in SEQ ID NO: 1 is provided by modifying lysine in the original sequence. The modification position 102 in FIG. 1 represents the position of glutamic acid at position 91 in each subunit.

In Examples described later, ferritin used in the present invention is designated as "Fer8-98glu". In the case of apoferritin, it is designated as "apoFer8-98glu".

Herein, there is the difference in the numerical notation by 7 between the number in designation ("98" in "Fer8-98glu") and the modification position (position 91) because the sequence employed as a standard of the designation is an amino acid sequence translated from a naturally occurring DNA sequence (herein, designated as sequence of "Fer0"), and is not a sequence of Fer8 (sequence excluding 7 amino acids of from the second to the eighth, from Fer0 sequence; SEQ ID NO: 3), which is employed as a basis herein. For reference, naturally occurring L chain of ferritin derived from horse is neither Fer0 nor Fer8, but ferritin excluding 8 amino acids of from the first to the eighth. General ferritin does not have this amino acid sequence. In addition, as would be understood from Comparative Examples described later, the effect of the present invention is not achieved with the amino acid sequence other than SEQ ID NO: 1 even though substitution of the amino acid that is present on the external side surface but not at position 91 is conducted.

As the amino acid present on the external side surface of ferritin, position 152, position 150, position 98 and the like can be included in addition to the position 91 (see, for example, tertiary structure registered in PDB ID code: 1DAT of Protein Data Bank (PDB)). Among these, the amino acid at position 91 is substituted with glutamic acid in the present invention, as described above.

The modified ferritin of the present invention can include an iron oxide particle inside as a core. The iron oxide particle can be utilized as a mask for forming a nanopillar structure by etching the substrate after the arrangement on the substrate, or as a catalyst for allowing a carbon nanotube to be lengthened. Alternatively, the iron oxide particle can be also subjected to application of forming electrically conductive nanoparticles following reduction.

As the substrate, a silicon substrate can be used. A silicon oxide film of high quality for use as a substrate can be formed by thermal oxidation of the silicon substrate surface.

It is desired that the substrate surface be negatively charged except for the region on which the molecular film is formed. In particular, a silicon oxide film surface is preferred since a great surface negative charge density in an aqueous solution can be stably provided.

In the molecular film having an amino group of the present invention, an aminosilane molecule is preferably used since an even and fine thin film spot can be formed on the SiO$_2$ surface. As the aminosilane molecule, for example, 3-aminopropyltriethoxysilane (hereinafter, may be abbreviated as "APTES") can be used.

After arranging ferritin, the decomposition step in which the substrate is heated to decompose the protein enables the inorganic particle within ferritin to be left on the substrate in the state as arranged, while concomitantly removing the protein portion present on the external side of the ferritin and the molecular film.

Embodiment 1

Hereinafter, Embodiments of the present invention are explained in more detail.

In this Embodiment 1, synthesis, extraction and purification of a recombinant apoferritin, and introduction of iron oxide therein and the following purification are explained. In particular, possibility of introduction of iron oxide inside the recombinant apoferritin when the amino acid present on the external side surface was substituted with glutamic acid was investigated. Starting from the conclusion, substitution of the amino acid at position 152 present on the external side surface with glutamic acid leads to failure in introduction of iron oxide inside.

Synthesis of apoFer8

First, apoFer8 was synthesized and purified according to the following procedure.

In production of recombinant apoferritin, a known gene recombinant technique and a protein expression process were used as explained below. First, a DNA fragment encoding the amino acid sequence of apoferritin was excised using an appropriate restriction enzyme, from a plasmid Takeda99224 (see, S. Takeda et al., Biochim. Biophys. Acta., 1174, 218-220, 1993) produced by Takeda, into which an apoferritin DNA derived from horse liver had been incorporated. Next, this DNA fragment was inserted into pMK-2 that is a vector plasmid for protein expression, whereby a plasmid for apoferritin expression was produced.

Subsequently, using this plasmid for apoferritin expression as a template, and a single strand DNA fragment into which desired mutation was incorporated as a primer, PCR (polymerase chain reaction) was performed to introduce desired mutation in a site specific manner at a target position of the DNA encoding the amino acid of apoferritin. Accordingly, a plasmid including a fragment of DNA of the mutant apoferritin gene having deletion of the DNA corresponding to a part encoding the amino acids of from the second to the eighth position of apoferritin. The DNA fragment of this apoferritin gene may be excised and incorporated into other vector plasmid if necessary.

Subsequently, thus produced plasmid was introduced into commercially available *Escherichia coli* (a kind of *E. coli*, Nova Blue). Following transformation, this *E. coli* was cultured in a large scale using a jar fermenter (apparatus for large-scale culture) at 37° C. Since the transformed *E. coli* is resistant to ampicillin, it can be selected by distinguishing from untransformed *E. coli* using resistance to ampicillin as a marker. In this *E. coli*, the recombinant apoferritin DNA incorporated into the plasmid was expressed, and thus apoferritin having deletion of from the second to the eighth amino acid residues was produced in large quantity. This modified apoferritin was designated as apoFer8. The amino acid sequence of apoFer8 is set out in SEQ ID NO: 3. Further, a product yielded by introducing a core into apoFer8 was designated as Fer8. According to the procedure described later, apoFer8 was extracted and purified from the bacterial body of *E. coli*.

Synthesis of apoFer8-98glu, apoFer8-159glu, apoFer8-157glu, and apoFer8-98glu105glu Next, in order to produce apoFer8-98glu, PCR was performed using as a template a plasmid into which a DNA encoding the amino acid sequence of apoFer8 (SEQ ID NO: 3) obtained by the aforementioned operation was incorporated, with an oligo DNA primer in which lysine (Lys) at position 91 in SEQ ID NO: 3 was substituted with glutamic acid (Glu).

As a result, the DNA having the sequence set out in SEQ ID NO: 2 was obtained. This DNA sequence encodes the amino acid sequence of apoFer8-98glu (SEQ ID NO: 1).

Next, by a similar operation to that for production of apoFer8, a plasmid into which the aforementioned DNA was inserted was produced. Thus resulting plasmid was introduced into *E. coli* (Nova Blue), and transformation was permitted. After the transformed *E. coli* was cultured in a large scale, apoFer8-98glu was extracted and purified from the bacterial body of *E. coli* according to the procedure described later.

Then, apoFer8-159glu having the amino acid sequence set out in SEQ ID NO: 4 in which glutamine (Gln) at position 152 in SEQ ID NO: 3 was substituted with glutamic acid (Glu) was obtained according to a similar procedure thereafter.

Also, apoFer8-157glu having the amino acid sequence set out in SEQ ID NO: 5 in which glycine (Gly) at position 150 in SEQ ID NO: 3 was substituted with glutamic acid (Glu) was obtained.

Further, apoFer8-98glu105glu having the amino acid sequence set out in SEQ ID NO.: 6 in which lysine (Lys) at position 91 and position 98 in SEQ ID NO: 3 was both substituted with glutamic acid (Glu) was obtained.

In the present invention, once a DNA encoding the altered apoferritin is obtained, this DNA can be amplified by a known technique. Therefore, when recombinant apoferritin is produced in large quantities, to carry out a recombination step of the gene again is not needed.

Extraction and Purification of Mutant Apoferritin

Extraction and purification procedures of mutant apoferritin were as follows. First, culture mixture of *E. coli* after completing the culture was transferred to a centrifuge tube, which was placed in a centrifuge. *E. coli* bacterial body was precipitated by centrifugal separation under a condition of 10,000 revolutions/min at 4° C. for 25 min. Next, after the precipitated bacterial body was collected, it was crushed in a liquid using an ultrasonic disintegrator to allow apoferritin to be eluted in the liquid.

Subsequently, the liquid including the crushed bacterial body was transferred to a centrifuge tube, which was placed in a centrifuge. The bacterial body which remained uncrushed was precipitated by centrifugal separation under a condition of 10,000 revolutions/min at 4° C. for 25 min.

Furthermore, the supernatant (supernatant liquid) was collected from the centrifuge tube, and the liquid was subjected to a heat treatment at 60° C. for 15 min. Thereafter, the mixture was transferred to a centrifuge tube, and centrifuged under a condition of 10,000 revolutions/min at 4° C. for 25 min.

According to this manipulation, unwanted proteins were denatured and precipitated at the bottom of the tube. Subsequently, after the supernatant was collected from the centrifuge tube, column chromatography was performed using Q-sepharose HP (anion exchange column) at 25° C., and thus the apoferritin fraction included in the supernatant was collected. This apoferritin fraction was further loaded on Sephacryl S-300 (gel filtration column) at 25° C., and purified by performing column chromatography. Impurities were removed by this manipulation, whereby purified recombinant apoferritin was obtained.

Introduction of Iron Oxide Core

Next, operation for introducing an iron oxide (ferrihydrite) core into apoferritin is explained in the following.

First, a ferritin solution was prepared by mixing each solution of HEPES buffer, an apoferritin solution, and an ammonium ferric sulfate $(Fe(NH_4)_2(SO_4)_2)$ solution in this order. In this ferritin solution, final concentrations were 250 mmol/L (pH 7.0) for HEPES buffer, 0.5 mg/mL for apoferritin, and 5 mmol/L for ammonium ferric sulfate, respectively. The entire manipulation process for preparing ferritin was carried out at 4° C.

Next, in order to complete the reaction of incorporating the iron ion inside apoferritin, and the oxidative reaction of the incorporated iron, the ferritin solution was left to stand overnight. According to this operation, iron oxide having a uniform size was introduced into a retentive portion of apoferritin to produce ferritin (complex of apoferritin with minute particle).

Next, the ferritin solution was charged into a vessel, and centrifuged under a condition of 10,000 revolutions per min for 15-30 min using a centrifuge, thereby removing the precipitate. Subsequently, the supernatant liquid after removing the precipitate was further centrifuged under a condition of 10,000 revolutions per min for 30 min.

In this procedure, dissolvable ferritin was dispersed in the supernatant liquid, while aggregated ferritin was precipitated to form an assembly.

With respect to the Fer8-98glu solution obtained using apoFer8-98glu following introduction of the iron oxide core, and the Fer8-159glu solution obtained using apoFer8-159glu following introduction of the iron oxide core, the states of the solution were photographed.

Purification of Ferritin Including Iron Oxide Core Introduced Therein

Next, the solvent of this supernatant liquid was concentrated using an ultrafilter Amicon Ultra-15 (NMWL: 50,000), and thus concentrated ferritin fraction was further purified by performing column chromatography by loading on Sephacryl S-300 (gel filtration column) which had been equilibrated with a 50 mmol/L Tris buffer at 25° C.

Accordingly, an eluate in which aggregates of ferritin particles were excluded by the gel filtration column was obtained.

The results are as in the following Examples.

Example 1

Figure 2:
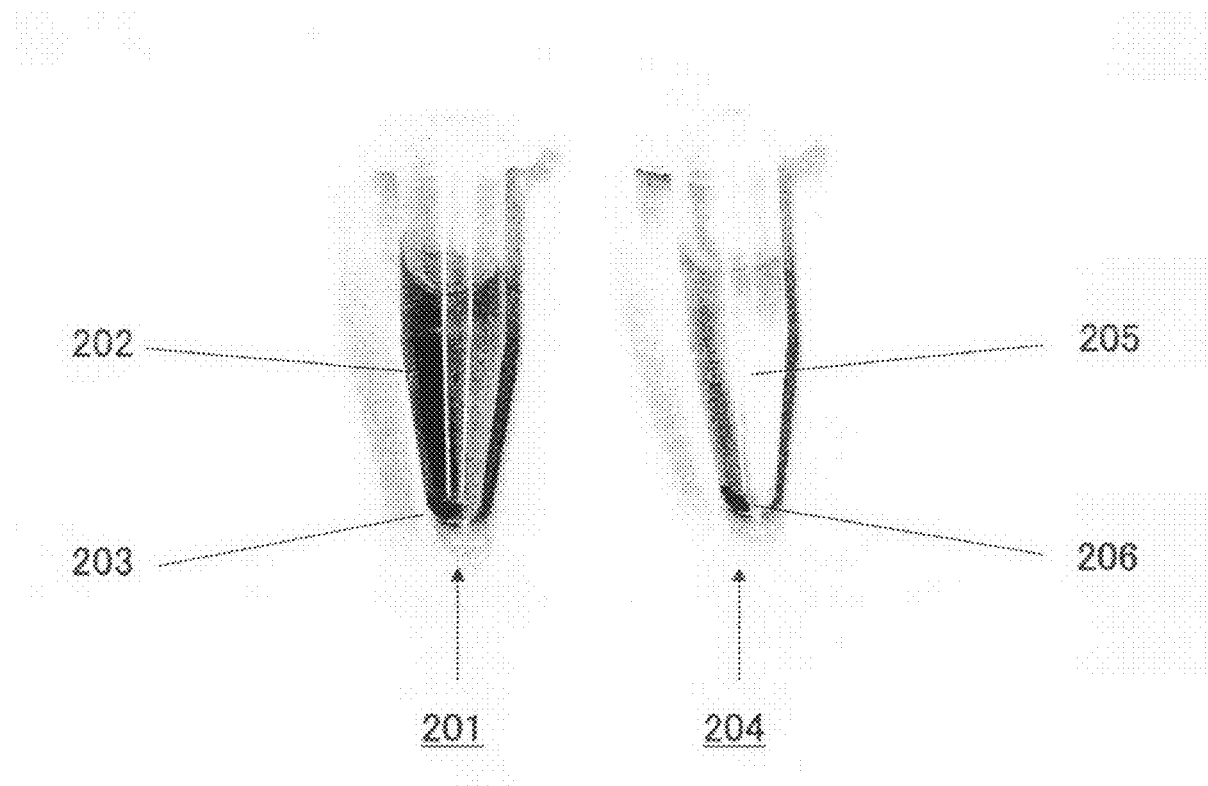
FIG. 2 shows a photograph illustrating the state of introduction of an iron oxide core into ferritin obtained in Example 1 and Comparative Example 1.

A photograph showing Fer8-98glu solution 201 after introducing the iron oxide core, obtained using apoFer8-98glu is presented in FIG. 2, left side. Although a small amount of Fer8-98glu precipitate 203 was found at the bottom of the Fer8-98glu solution 201, supernatant liquid 202 of Fer8-98glu exhibited a dark color (yellowish brown) through absorbing the visible light. This result suggests that a large quantity of ferritin was dispersed or dissolved without aggregation even after the introduction of the core. When the ferritin into which the iron oxide core was introduced was purified, Fer8-98glu was recovered in the eluate.

Comparative Example 1

A photograph showing Fer8-159glu solution 204 after introducing the iron oxide core, obtained using apoFer8-159glu is presented in FIG. 2, right side. A larger quantity of Fer8-159glu precipitate 206 was found at the bottom of Fer8-159glu solution 204 as compared with the Fer8-98glu precipitate 203. In addition, the liquid color of Fer8-159glu supernatant liquid 205 was lighter than the liquid color of Fer8-98glu, and was almost colorless and transparent. This result suggests that almost all Fer8-159glu aggregated and precipitated along with the introduction of the core, and was not thus dissolved. When the ferritin into which the iron oxide core was introduced was purified, Fer8-159glu was not recovered in the eluate.

It is necessary to recover the purified ferritin and to disperse or dissolve it in an aqueous solution for arranging ferritin on the substrate; therefore, apoFer8-159glu cannot be utilized in the arrangement on the substrate.

The results described above are summarized in Table 1.

TABLE 1

| | Fer8-98glu | Fer8-159glu |
|---|---|---|
| Results of purification after introducing iron oxide core | ○ | x |

In Table 1, "○" indicates that ferritin was recovered in the eluate after the purification, while "x" indicates that it was not recovered.

The results suggest that for use in arrangement of ferritin on the substrate, mere substitution of the amino acid on the external side surface with glutamic acid is not satisfactory, but a precipitate may be yielded in forming the core inside, depending on the position of the substitution. With respect to each ferritin of Fer8, Fer8-157glu and Fer8-98glu105glu, successful introduction of the iron core into the apoferritin, purification and recover could be achieved without problems, similarly to Fer8-98glu.

Embodiment 2

In this Embodiment 2, sole arrangement rate of each recombinant ferritin was investigated. Starting from the conclusion, sole arrangement rate of Fer8-98glu set out in SEQ ID NO: 1 was significantly higher than the sole arrangement rate of other recombinant ferritin. Further, the sole arrangement rate of the other recombinant ferritin was lower than that of Fer8.

First, the iron oxide core was introduced according to the same steps of Embodiment 1. Next, the ferritin into which the iron oxide core was introduced was recovered and purified according to the step described below, followed by formation of molecular film spot on the substrate surface, on which ferritin was arranged finally.

Recovery and Purification of Ferritin Including Iron Oxide Core Introduced Therein Next, the solvent of this supernatant liquid was concentrated using an ultrafilter Amicon Ultra-15 (NMWL: 50,000), and thus concentrated ferritin fraction was further purified by performing column chromatography by loading on Sephacryl S-300 (gel filtration column) which had been equilibrated with a 50 mmol/L Tris buffer at 25° C.

The gel filtration column excluded aggregates of ferritin particles, and thus sole ferritin including iron oxide therein was obtained.

Formation of Molecular Film Spot on Substrate Surface

Formation of molecular film spot on the substrate surface is explained with reference to FIG. 3.

First, p-type silicon substrate 301 was oxidized to form silicon oxide film 302 having a thickness of 3 nm on the surface thereof.

Next, after washing the substrate with pure water, UV light/ozone was irradiated for 10 min while the substrate was kept in the state of the temperature being 110° C. Accordingly, washing and hydrophilizing treatment of the surface of the substrate was completed.

Then, an electronic beam resist (manufactured by Nippon ZEON Co., Ltd., ZEP 520A) was applied on the substrate following the hydrophilizing treatment.

Further, electron beam lithography was carried out on the substrate on which electron beam resist film 303a was applied using an electronic beam lithography exposure apparatus (Elionix ELS-7500).

Upon the lithography, (A) square×7.5 nm, (B) square×12.5 nm, (C) circle f20 nm, and (D) circle f23 nm as the lithography shape were drawn on the substrate with the electronic beam to apply the accelerating voltage being 50 kA, and the beam electric current value being 20 pA.

Figure 3:
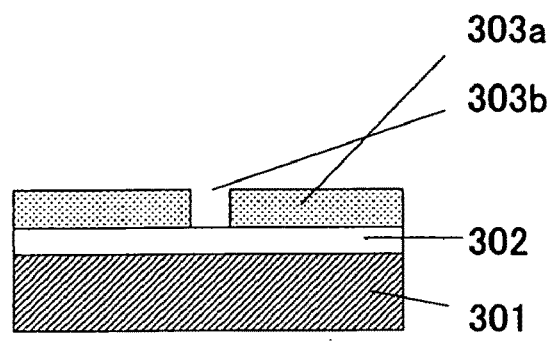
FIG. 3 shows a view illustrating steps in the method of arranging ferritin.
Figure 3:
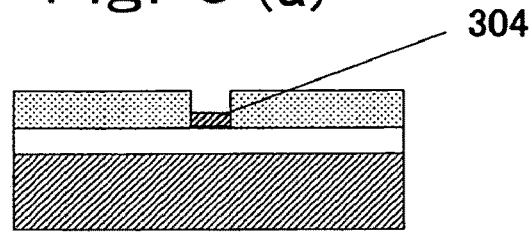
Figure 3:
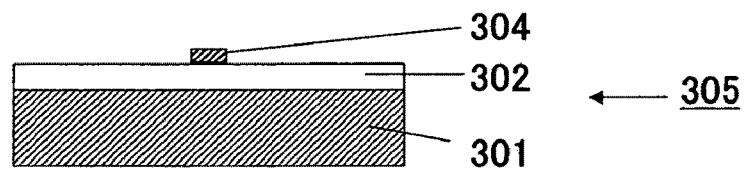
Figure 3:
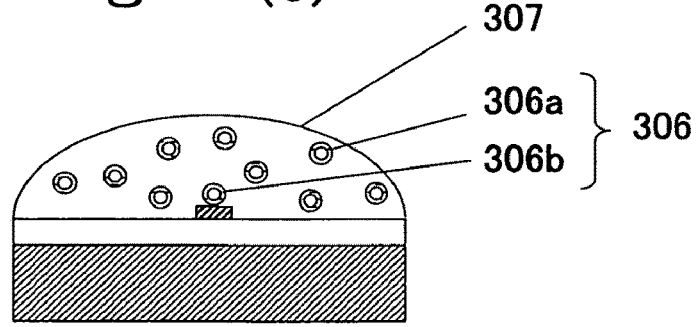
Figure 3:
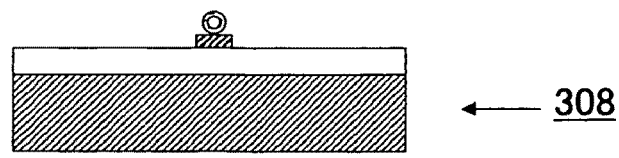

Following the lithography, electron beam resist spot (resist opening) 303b was formed by development with amyl acetate (n-amyl acetate) (FIG. 3 (a)).

A hydrophilic surface of the silicon oxide film appeared on the bottom of each spot opening. A part of thus produced electron beam resist spot 303b was observed with a scanning electron microscope apparatus (SEM), and the diameter was measured.

The areas of spot A, spot B, spot C and spot D formed with the lithography shapes (A), (B), (C) and (D), respectively, were 380 nm$^2$, 710 nm$^2$, 1,600 nm$^2$ and 2,100 nm$^2$, respectively (all circular, diameter: 22 nm, 30 nm, 45 nm and 52 nm).

In a sealable vessel were placed the aforementioned substrate, and 3-aminopropyltrimethoxysilane (APTES) as an aminosilane molecule. When the vessel was kept with sealing tight at room temperature for 3 to 5 hrs, the substrate surface reacted with the aminosilane molecule, whereby molecular film spot (molecular film modified region) 304 having an amino group was formed (FIG. 3 (b)).

The substrate was washed with dehydrated ethanol, and immersed in dimethylacetamide kept at 40° C. for 5 min, followed by ultrasonic washing for 5 min to give substrate 305 provided with fine molecular film spots having a film thickness of about 10 Å (FIG. 3 (c)).

Since the molecular film spot 304 as described above is small in both film thickness and size, direct measurement of its size is difficult and accompanied by a large extent of error. However, since its shape corresponds to the shape of the electron beam resist spot 303b, evaluation of its size can be made easily and accurately by measuring the size of the electron beam resist spot 303b.

The diameter of the molecular film spot determined on SEM observation by staining the molecular film spot with a PTA (phosphotungstic acid) solution agreed with the diameter of the resist spot within the range of the measurement error (2 to 5 nm) due to resolution limitation of the observed SEM image.

In the electron beam resist spot 303b, the region where the electronic beam was irradiated upon SEM observation had an altered surface state; however, other region without being affected by the SEM observation can be utilized in the following process.

Arrangement of Ferritin

Ferritin solution 307 was prepared which included 0.5 mg/mL of ferritin 306 according to the recovery and purification of ferritin to which the iron oxide core was introduced as described above. To the aqueous solution were added MES (2-(4-morpholino)ethanesulfonic acid) and Tris(2-amino-2-(hydroxymethyl)-1,3-propanediol) as a buffering agent to make the pH 7. The concentrations of MES and Tris were identical, and the solution had a pH of 7. The concentration of the buffering agent will be described later, but reference of, for example, "buffering agent concentration being 0.1 mM" means that the concentrations of MES and Tris in the solution are both 0.1 mM. The ferritin in the solution was concentrated as needed, using an ultrafilter and an ultracentrifugation device, and then diluted with a solution containing the buffering agent having an intended concentration. By repeating this manipulation of concentration and dilution five to ten times, the buffering agent was replaced, and the concentration was adjusted.

The aforementioned ferritin solution 307 was added dropwise on the substrate 305 having the molecular film spot produced by forming the molecular film spot on a substrate surface as described above, and stood still at room temperature for 1 min. In this procedure, a part of ferritin in the solution was adsorbed on the molecular film spot on the substrate (306b).

Thereafter, the substrate was washed with running pure water for 5 min to remove excess unadsorbed ferritin 306a. The substrate after washing was dried, and baked at 110° C. for 3 min to immobilize the adsorbed ferritin 306b on the substrate. Accordingly, substrate 308 provided with ferritin minute particles adsorbed and immobilized on the molecular film spot 304 was obtained. The surface of the substrate 308 was observed with SEM.

In this Embodiment 2, aiming at improvement of reproducibility of arrangement of single ferritin on the substrate, in particular, the comparison was made under conditions to yield the highest reproducibility of sole arrangement using spot A or spot B with the buffering agent concentration of 0.1 mM or 0.01 mM.

The results are as demonstrated in the following Examples and Comparative Examples.

Example 2

Using Fer8-98glu and the spot B with the buffering agent concentration of 0.1 mM, ferritin was arranged. A photograph shown in the appearance of the obtained sole arrangement of ferritin is presented in FIG. 4.

Figure 4:
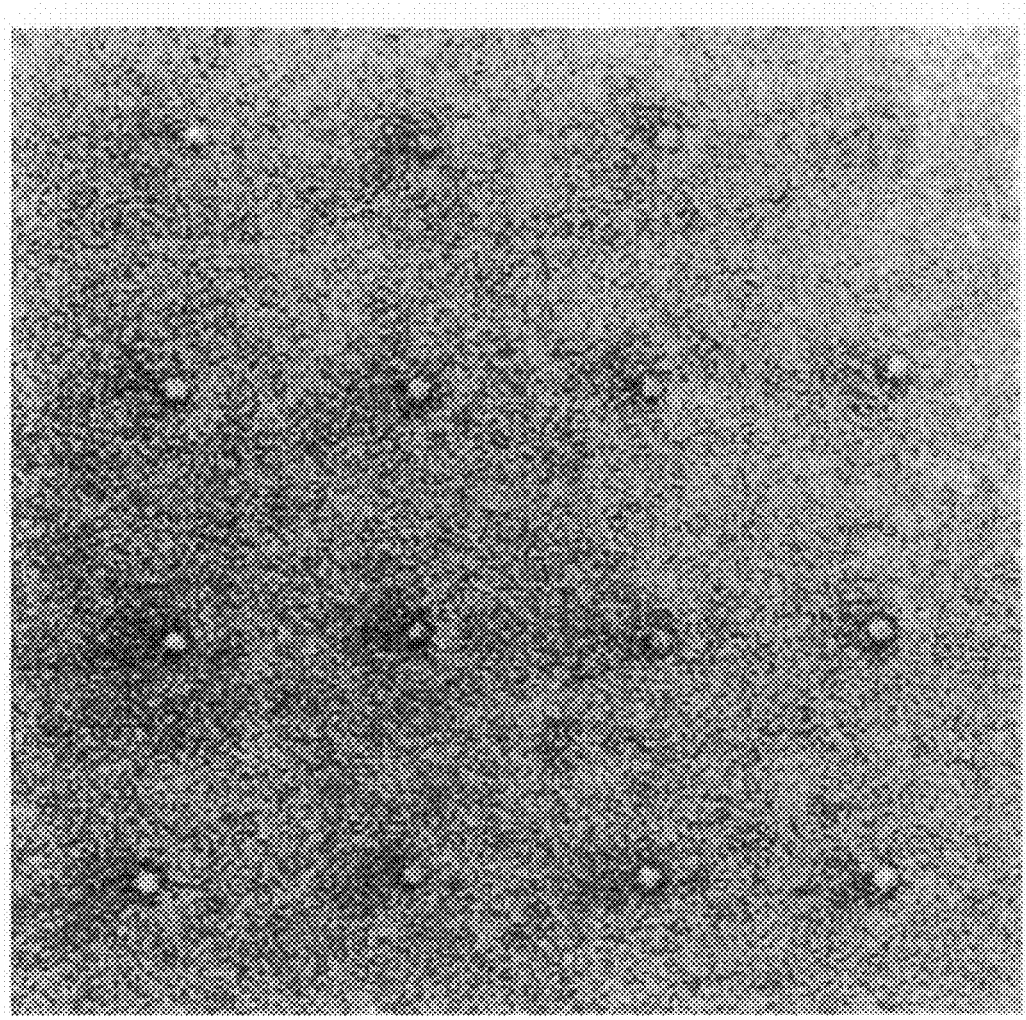
FIG. 4 shows a photograph illustrating the state of arrangement of ferritin obtained in Example 2.

In FIG. 4, sole arrangement with high reproducibility could be ascertained, and sole ferritin was fixed on almost all the molecular film spots. The sole arrangement rate in FIG. 4 was 94%.

Comparative Example 2

Using Fer8 and the spot A with the buffering agent concentration of 0.01 mM, ferritin was arranged. A photograph shown in the appearance of the obtained sole arrangement of ferritin is presented in FIG. 5.

Figure 5:
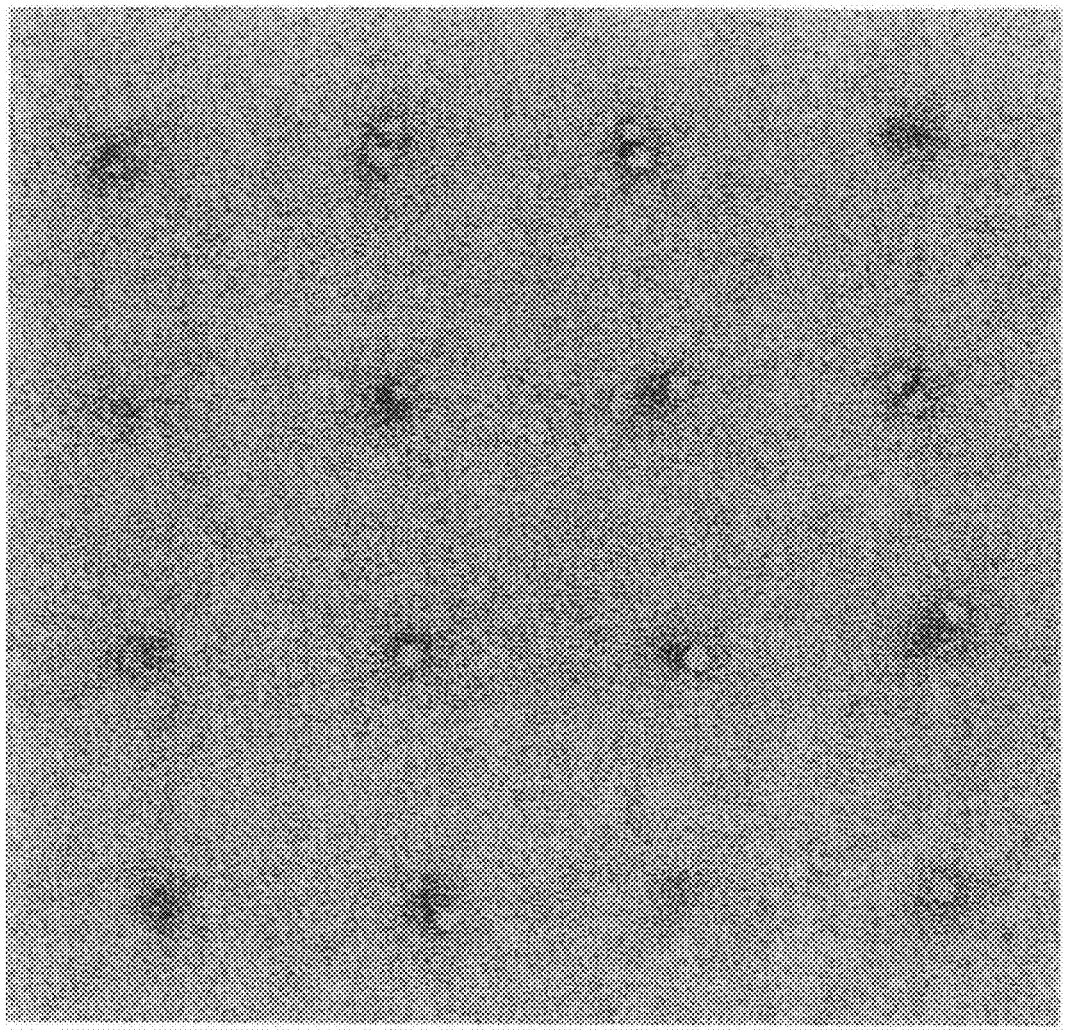
FIG. 5 shows a photograph illustrating the state of arrangement of ferritin obtained in Comparative Example 2.

In FIG. 5, it is proven that reproducibility of the arrangement was inferior, and that although sole arrangement was found on a part of the spot, the spots with double arrangement and the spots with no arrangement of ferritin were present in multiple numbers, respectively. The sole arrangement rate in FIG. 5 was 63%.

It should be noted that a large quantity of Fer8 was adsorbed on the spot B, and thus sole arrangement was not achieved in both cases of the buffering agent concentration being 0.1 mM and 0.01 mM. Also in the case in which the buffering agent concentration was 0.1 mM on the spot A, a large number of Fer8 was adsorbed, whereby sole arrangement was not achieved.

Comparative Example 3

Using Fer8-157glu and the spot A with the buffering agent concentration of 0.01 mM, ferritin was arranged. A photograph shown in the appearance of the obtained sole arrangement of ferritin is presented in FIG. 6.

Figure 6:
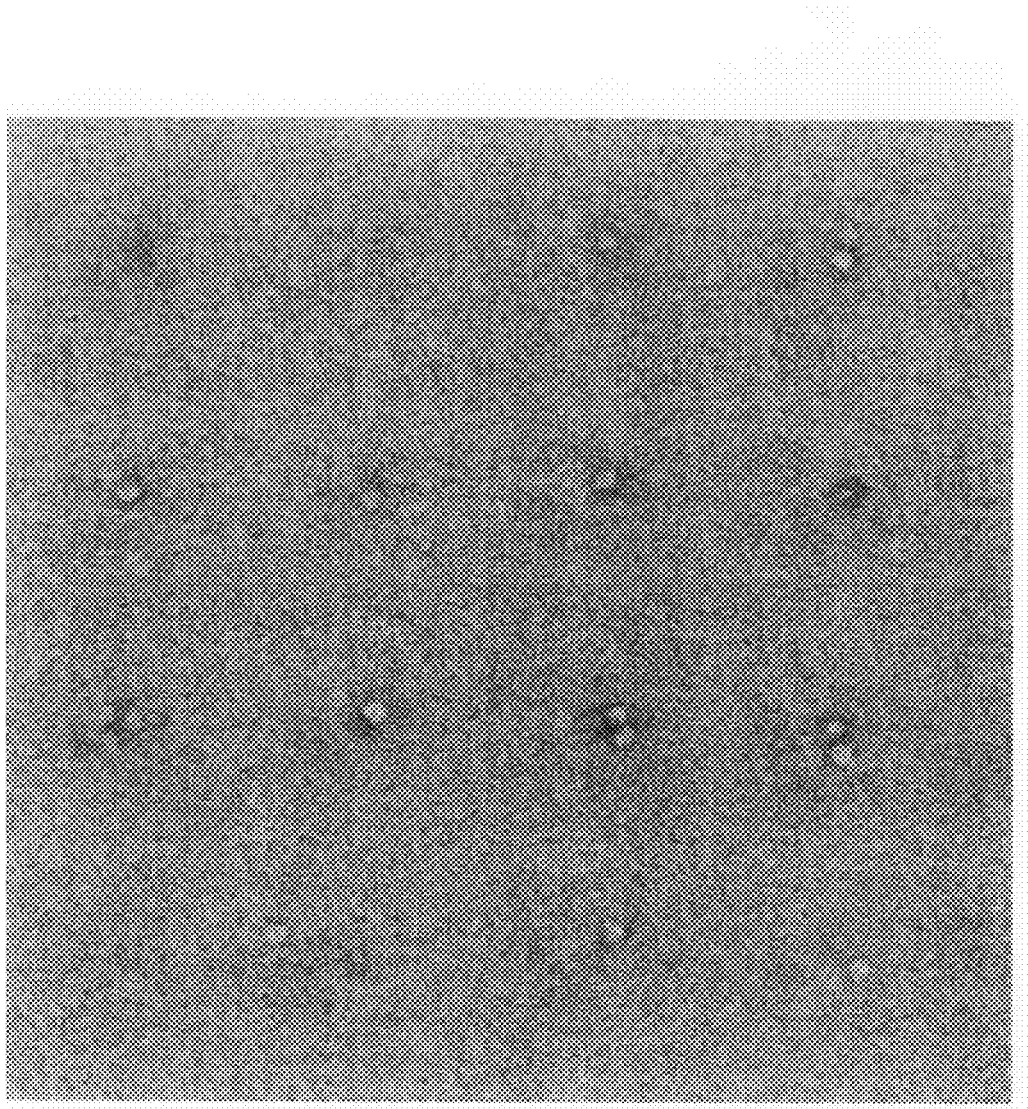
FIG. 6 shows a photograph illustrating the state of arrangement of ferritin obtained in Comparative Example 3.

Also in FIG. 6, it is proven that reproducibility of the arrangement was inferior, and that although sole arrangement was found on a part of the spot, the spots with double arrangement and the spots with no arrangement of ferritin were present in multiple numbers, respectively. The sole arrangement rate in FIG. 6 was 50%.

It should be noted that a large quantity of Fer8-157glu was adsorbed on the spot B, and thus sole arrangement was not achieved in both cases of the buffering agent concentration being 0.1 mM and 0.01 mM. Also in the case in which the buffering agent concentration was 0.1 mM on the spot A, a large number of Fer8-157glu was adsorbed, whereby sole arrangement was not achieved.

Comparative Example 4

Using Fer8-98glu105glu and the spot A with the buffering agent concentration of 0.01 mM, ferritin was arranged. A photograph shown in the appearance of the obtained sole arrangement of ferritin is presented in FIG. 7.

Figure 7:
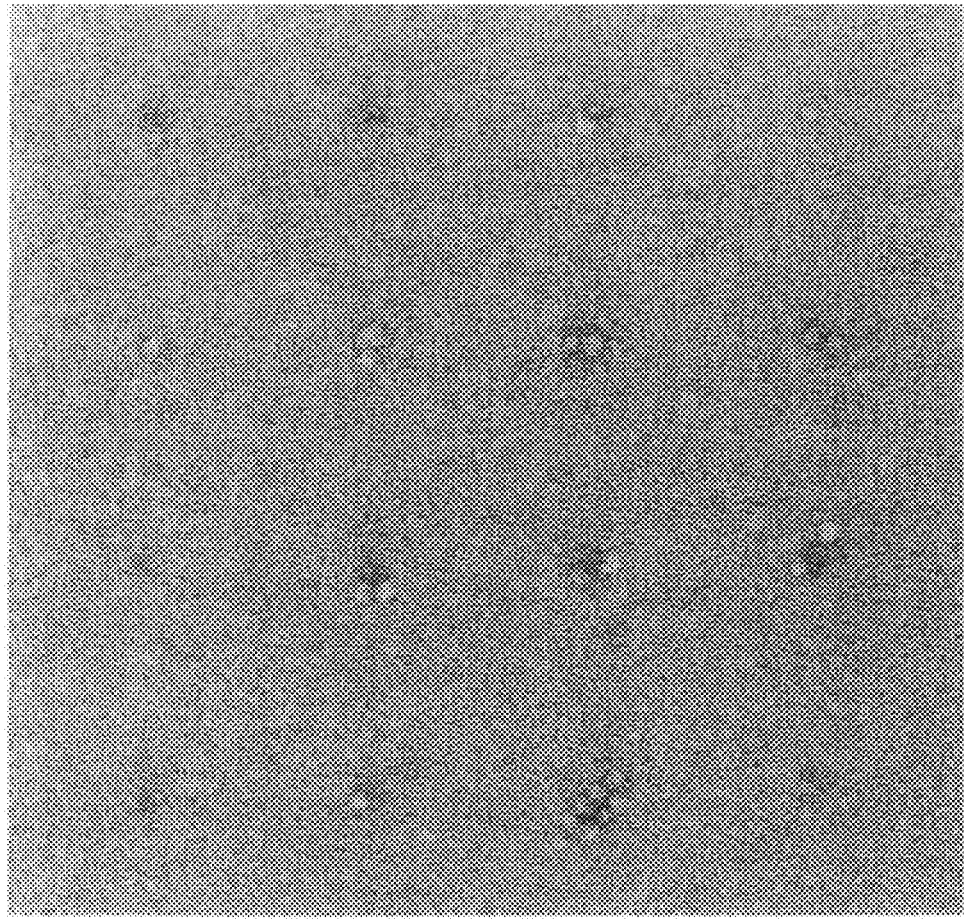
FIG. 7 shows a photograph illustrating the state of arrangement of ferritin obtained in Comparative Example 4.

Also in FIG. 7, it is proven that reproducibility of the arrangement was inferior, and that although sole arrangement was found on a part of the spot, the spots with double or more arrangement and the spots with no arrangement of ferritin were present in multiple number, respectively. The sole arrangement rate in FIG. 7 was 38%.

It should be noted that a large quantity of Fer8-98glu105glu was adsorbed on the spot B, and thus sole arrangement was not achieved in both cases of the buffering agent concentration being 0.1 mM and 0.01 mM. Also in the case in which the buffering agent concentration was 0.1 mM on the spot A, a large number of Fer8-98glu105glu was adsorbed, whereby sole arrangement was not achieved.

From the foregoings, results of determination of the sole arrangement rate when each ferritin was used are summarized in Table 2.

The term "sole arrangement rate" herein refers to a rate of the number of the molecular film spots on which sole ferritin molecule was arranged in effect, with respect to total number of the molecular film spots provided for arranging ferritin, and is thus a marker that indicates higher reproducibility as its value approximates 100%.

Herein, the term "sole arrangement rate" may be also referred to "reproduction rate", or "reproducibility".

TABLE 2

|  | Fer8-98glu | Fer8 | Fer8-157glu | Fer8-98glu105glu |
|---|---|---|---|---|
| Sole arrangement rate | 94% | 63% | 50% | 38% |

The results of Fer8 almost match to the results of arrangement according to the second prior art. To the contrary, the reproducibility for Fer8-98glu was significantly improved, and successful arrangement of sole ferritin molecule could be achieved at 90% or more arrangement positions. On the other hand, the reproducibility of Fer8-157glu was further deteriorated even though it was compared with unmodified Fer8.

With respect to Fer8-98glu105glu, irrespective of further increase of glutamic acid on the external side surface as compared with Fer8-98glu, yet inferior reproducibility than unmodified Fer8 was exhibited.

The foregoing results indicate that the reproducibility of sole arrangement was not improved by merely substituting the amino acid on the external side surface with glutamic acid, or by increasing the quantity of negative charge presented to the external side, and that the amino acid sequence set out in SEQ ID NO: 1 particularly had a specific effect.

As would be understood also from the results described above, it is necessary to use modified ferritin constructed with protein subunit having an amino acid sequence set out in SEQ ID NO: 1 in order to arrange the ferritin each one molecule at a target site on a substrate with superior reproducibility.

Embodiment 3

In this Embodiment 3, the size of the molecular film spot was investigated since arrangement of single ferritin on too large molecular film spots, i.e., those having a too great surface area, completely fails in use of any ferritin.

Also in this Embodiment, in a similar manner to Embodiment 2, introduction of the iron oxide core, recovery and purification of the ferritin into which the iron oxide core was introduced, and formation of molecular film spot on the substrate surface were carried out, then arrangement of ferritin was finally conducted.

However, in this Embodiment, in an attempt to arrange single ferritin on the molecular film spot having a greater area, sole arrangement probability for each ferritin was compared using the spot C or the spot D (see, Embodiment 2 with respect to the spot size), unlike Embodiment 2.

In any case in which the aforementioned ferritin was used, the state of adsorption was not altered even though the buffering agent concentration was lowered to less than 0.01 mM. To the contrary, when the buffering agent concentration was elevated to equal to or greater than 0.1 mM, the number of adsorbed molecules of ferritin increased, and thus sole arrangement probability was declined. Therefore, the buffering agent concentration of 0.01 mM was employed.

The results are as demonstrated in the following Examples and Comparative Examples.

Example 3

Figure 8:
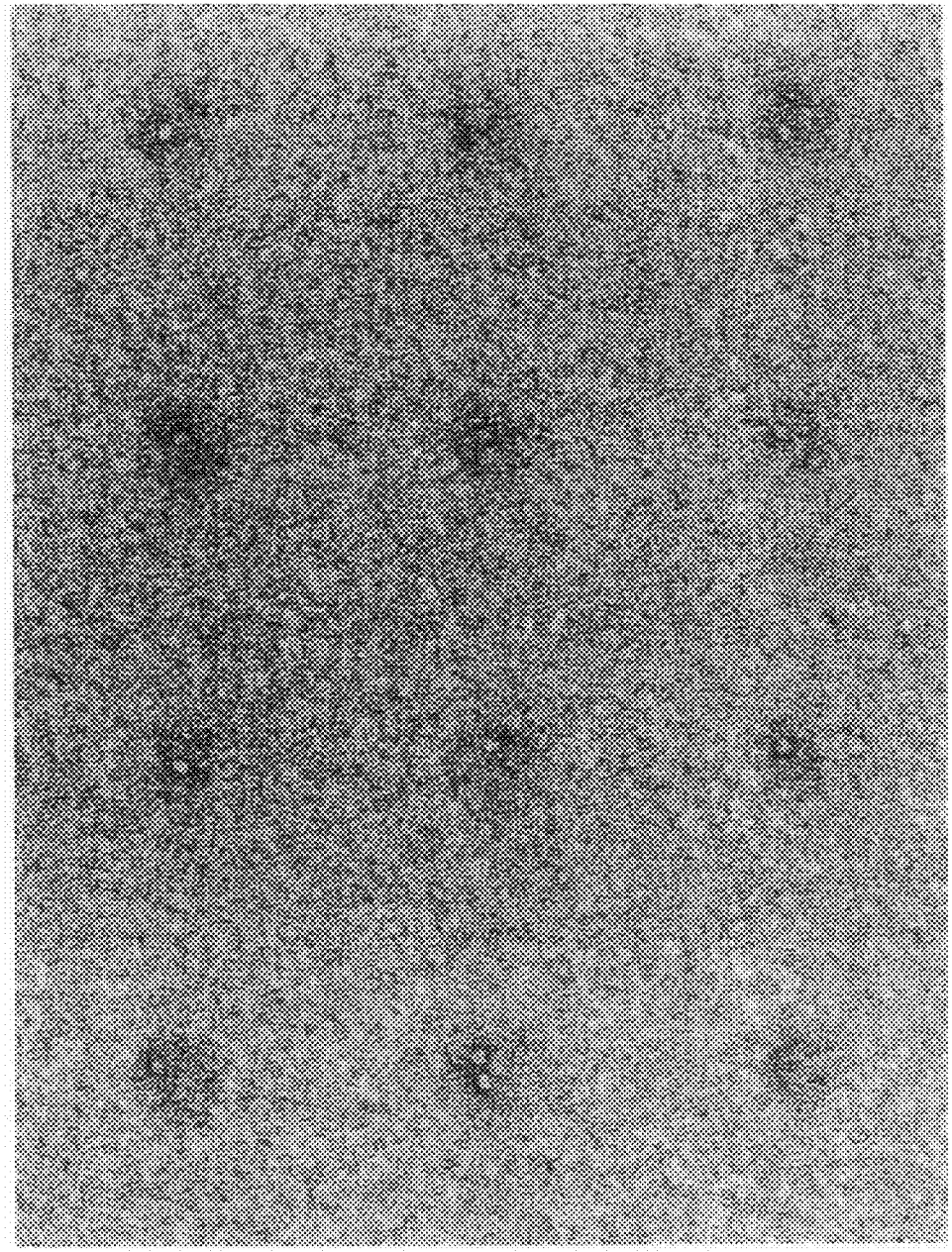
FIG. 8 shows a photograph illustrating the state of arrangement of ferritin obtained in Example 3.

A photograph showing the appearance of sole arrangement of ferritin obtained using Fer8-98glu and the spot C is presented in FIG. 8.

In FIG. 8, fixation of sole ferritin is illustrated on many molecular film spots. The average number of arrangement in FIG. 8 is 1.0.

Example 4

Figure 13:
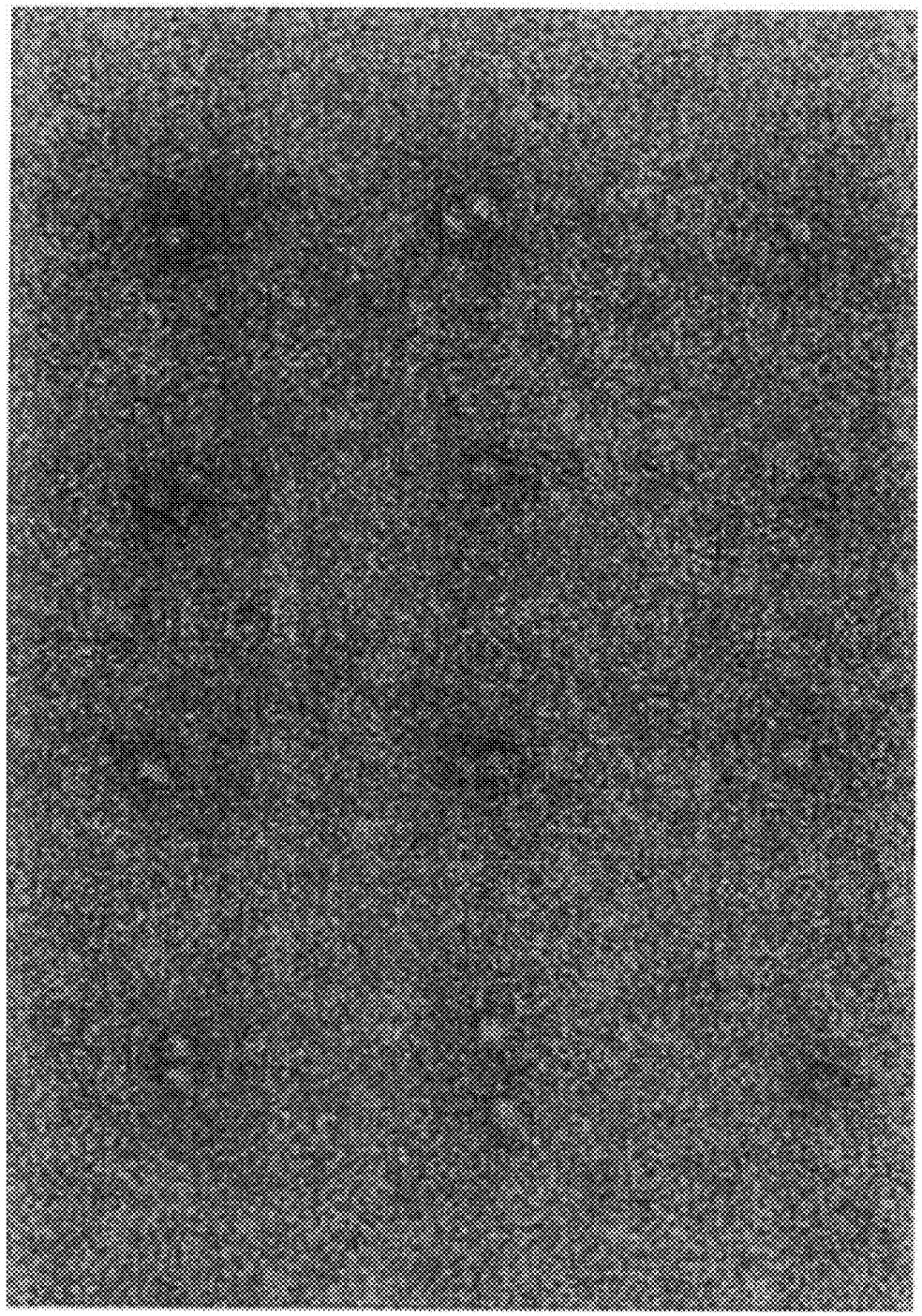
FIG. 13 shows a photograph illustrating the state of arrangement of ferritin obtained in Example 4.

A photograph showing the appearance of sole arrangement of ferritin obtained using Fer8-98glu and the spot D is presented in FIG. 13.

In FIG. 13, fixation of sole ferritin is illustrated on some molecular film spots, although there also exist the molecular film spots in which two molecules of ferritin were arranged. The average number of arrangement in FIG. 13 is 1.4.

Comparative Example 5

Figure 9:
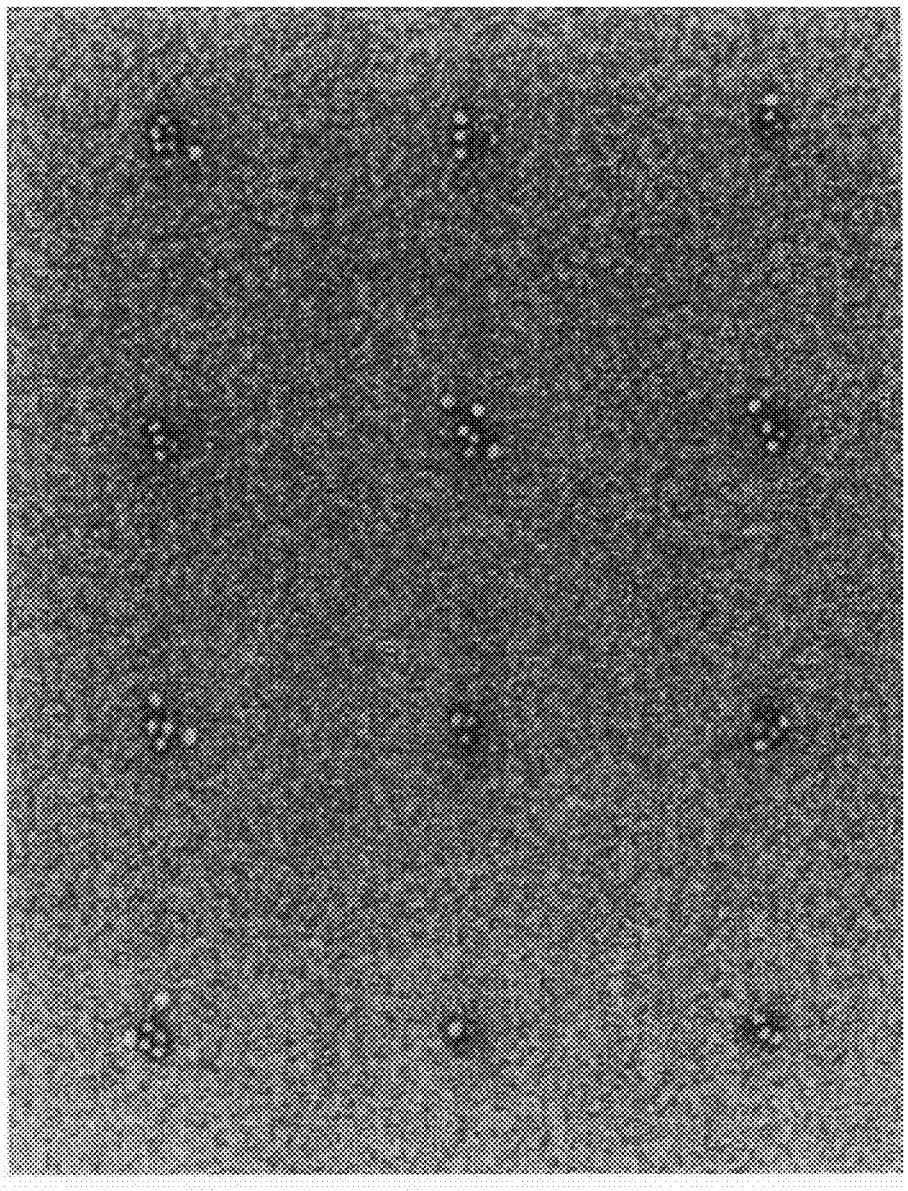
FIG. 9 shows a photograph illustrating the state of arrangement of ferritin obtained in Comparative Example 5.

A photograph showing the appearance of sole arrangement of ferritin obtained using Fer8 and the spot C is presented in FIG. 9.

In FIG. 9, low sole arrangement probability is suggested, and a plural number of molecules of ferritin were adsorbed on almost molecular film spots. The average number of arrangement in FIG. 9 is 4.2.

Comparative Example 6

Figure 10:
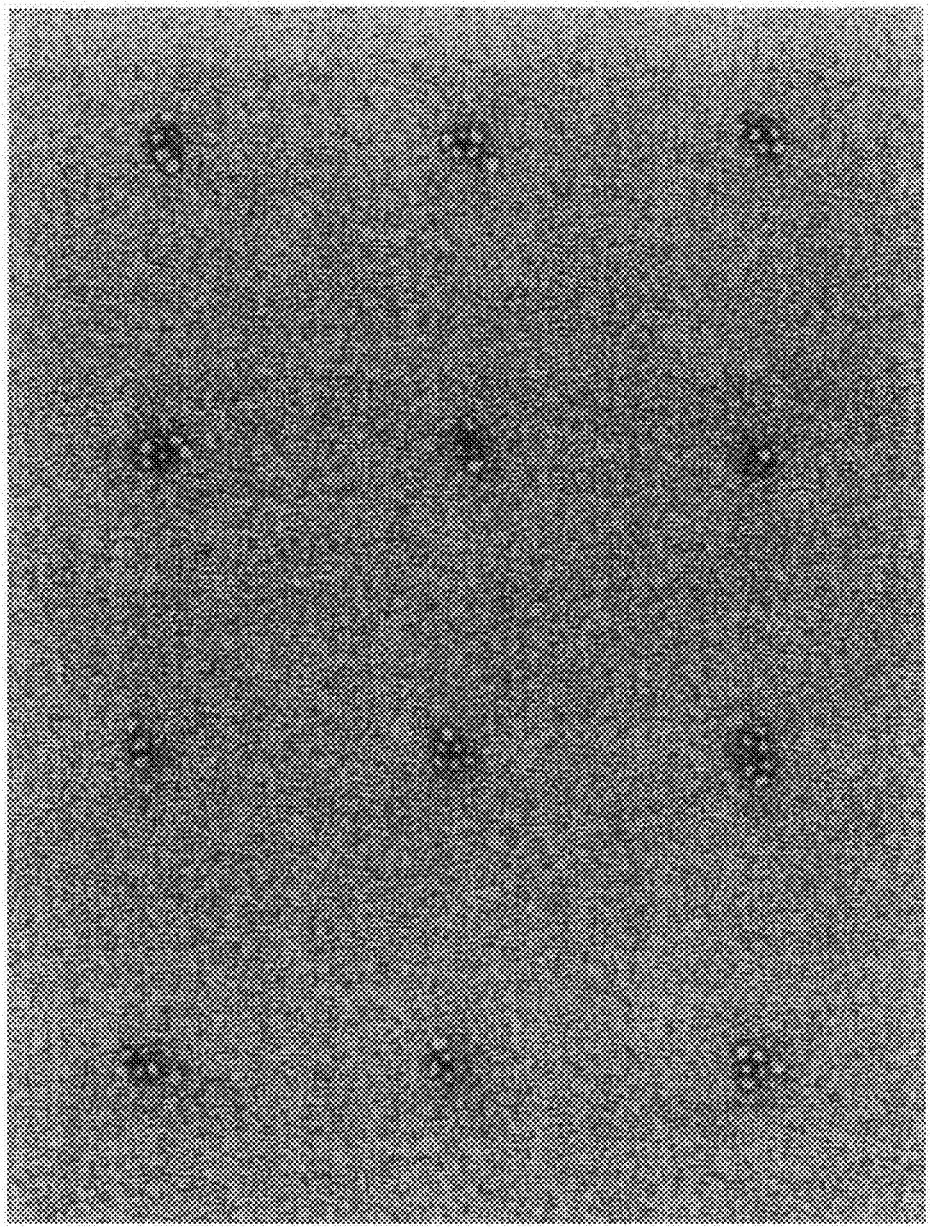
FIG. 10 shows a photograph illustrating the state of arrangement of ferritin obtained in Comparative Example 6.

A photograph showing the appearance of sole arrangement of ferritin obtained using Fer8-157glu and the spot C is presented in FIG. 10.

Also in FIG. 10, low sole arrangement probability is suggested, and a plural number of molecules of ferritin were adsorbed on almost molecular film spots. The average number of arrangement in FIG. 10 is 4.8.

Comparative Example 7

Figure 11:
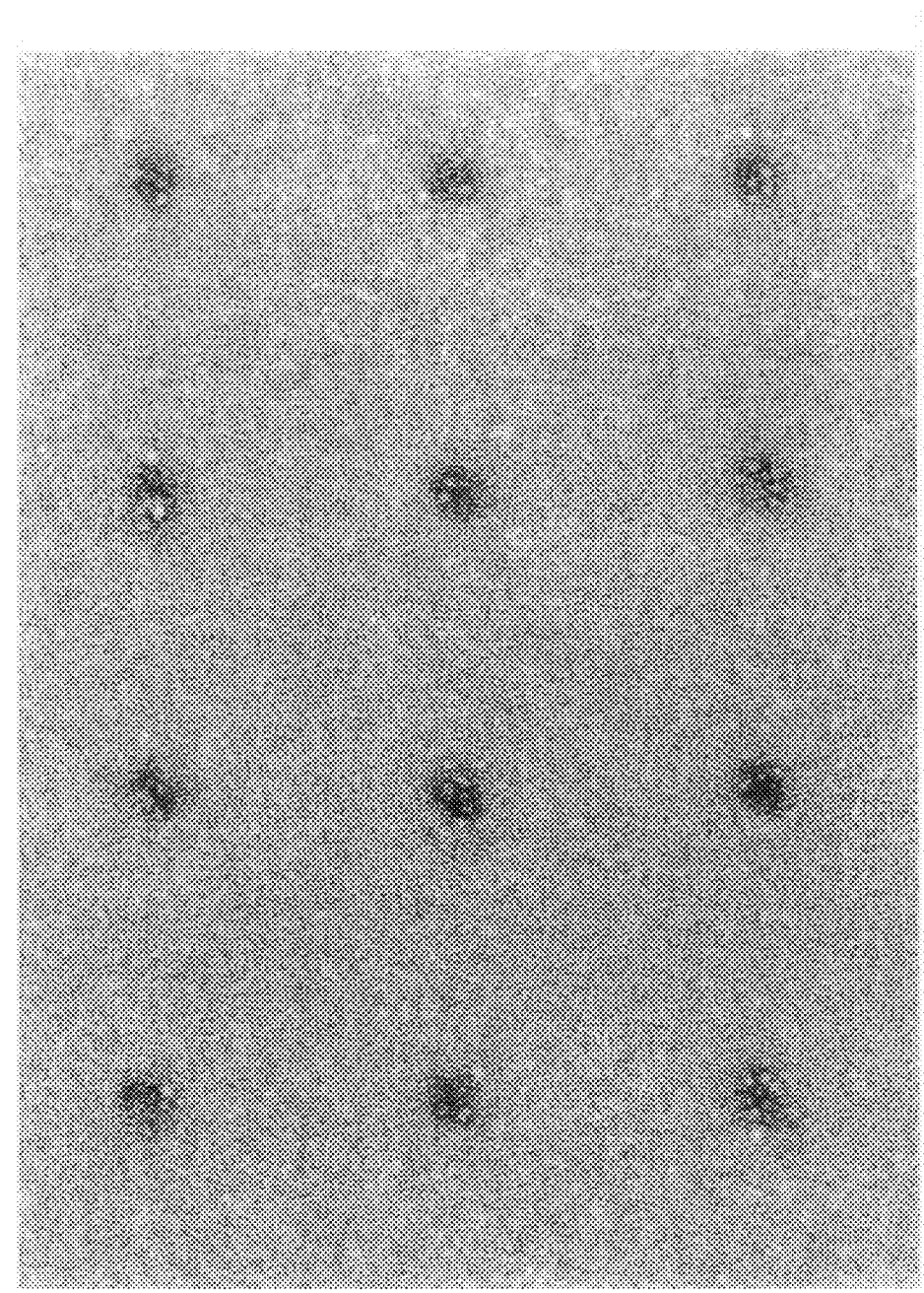
FIG. 11 shows a photograph illustrating the state of arrangement of ferritin obtained in Comparative Example 7.
Figure 12A:
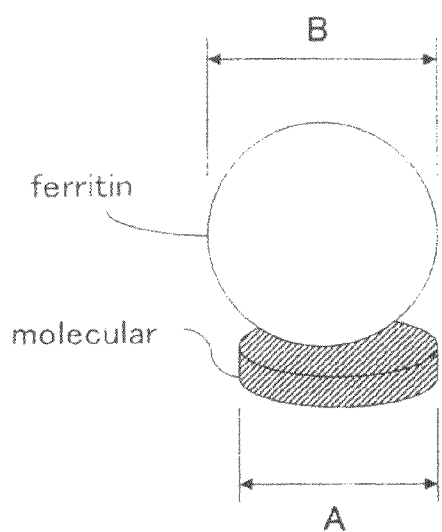
FIG. 12 shows a conceptual diagram illustrating the state of arrangement of ferritin on a molecular film spot.
Figure 12B:
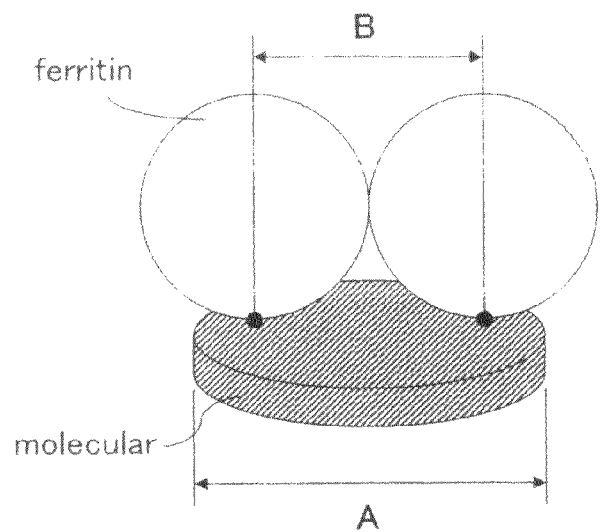

A photograph showing the appearance of sole arrangement of ferritin obtained using Fer8-98glu105glu and the spot C is presented in FIG. 11.

Also in FIG. 11, low sole arrangement probability is suggested, and a plural number of molecules of ferritin were adsorbed on almost molecular film spots. The average number of arrangement in FIG. 11 is 3.8.

From the foregoings, the results of determination of average number of arrangement on the spot C when each ferritin was used are summarized in Table 3.

Herein, the average number of arrangement refers to a value derived through dividing total number of the ferritin molecules arranged on the molecular film spots, by the number of the molecular film spots, and is thus a marker that indicates more favorable sole arrangement as the value approximates 1.

TABLE 3

|  | Fer8-98glu | Fer8 | Fer8-157glu | Fer8-98glu105glu |
| --- | --- | --- | --- | --- |
| Average number of arrangement | 1.0 | 4.2 | 4.8 | 3.8 |

The results presented above indicate that sole arrangement on the spot D having a diameter of 45 nm cannot be achieved with the ferritin other than Fer8-98glu. In other words, as long as Fer8-98glu is employed, sole arrangement on the spot D having a diameter of 45 nm is enabled.

Even though modified ferritin, similarly to Fer8-98glu, having substitution of the amino acid on the external side with glutamic acid was used, the effects of the present invention cannot be exhibited when the modification position is different, or the number of the modified amino acid is increased.

As would be understood also from the results described above, it is necessary to use modified ferritin constructed with protein subunit having an amino acid sequence set out in SEQ ID NO: 1 in order to arrange the ferritin each one molecule at a target site on a substrate with superior reproducibility.

Embodiment 4

In this Embodiment 4, a method of arranging inorganic particles is explained.

Also in this Embodiment, introduction of the iron oxide core; recovery and purification of the ferritin into which the iron oxide core was introduced; formation of molecular film spot on the substrate surface; and arrangement of ferritin were carried out, in a similar manner to Embodiment 2 and Embodiment 3. Next, the protein was removed according to the following step.

Removal of Protein

The substrate on which ferritin was arranged was placed in a lamp heating furnace, and the furnace was vacuum drawn. An oxygen gas was supplied until the furnace reached to the ambient pressure (flow rate: 100 sccm).

Next, a heat treatment was performed by heating the substrate under a condition of ambient pressure, an oxygen gas flow rate of 100 sccm at 500° C. for 10 min.

After completing the heat treatment, a nitrogen gas was supplied at a flow rate of 10 L/m to cool the substrate. When the substrate temperature was lowered to equal to or less than 100° C., the substrate was taken out from the furnace. Thus obtained substrate was observed with SEM.

The results are as demonstrated in the following Example.

Example 4

In a similar manner to Example 2, the protein removal was conducted using the substrate on which ferritin was arranged with Fer8-98glu and the spot B, and with a buffering agent concentration of 0.1 mM. SEM observation could reveal that the iron oxide minute particle as a core was left on the substrate, while keeping the state of the sole nano dot arranged on each site of the arrangement.

Removal of the protein on the external side of ferritin under the condition of the heat treatment described above was verified otherwise by XPS (X-ray photoelectron spectroscopy) analyses of the substrate provided with ferritin on the entire face to be analyzed (Yoshii et al., Jpn. J. Appl. Phys. 44 (2005), 1518).

Supplement

The terms "single", "sole", and "one" used herein have the same meaning. The terms "modified ferritin", "mutant ferritin", and "recombinant ferritin" also have the same meaning. The terms "modified apoferritin", "mutant apoferritin", and "recombinant apoferritin" also have the same meaning.

From the foregoing description, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

The method of arranging ferritin, and the method of arranging inorganic particles according to the present invention are useful as a method of arranging minute particles on a substrate. These methods can be particularly utilized in applications such as, for example, semiconductor elements in which selective arrangement of minute particles on a specific site is particularly desired.

Free Text of Sequence Listing

<223> of SEQ ID NO: 1: modified ferritin derived from horse (apoFer8-98glu)

<223> of SEQ ID NO: 2: recombinant DNA of modified ferritin derived from horse (apoFer8-98glu)

<223> of SEQ ID NO: 3: modified ferritin derived from horse (apoFer8)

<223> of SEQ ID NO: 4: modified ferritin derived from horse (apoFer8-159glu)

<223> of SEQ ID NO: 5: modified ferritin derived from horse (apoFer8-157glu)<

<223> of SEQ ID NO: 6: modified ferritin derived from horse (apoFer8-98glu105glu)

Sequence Listing

DESCRIPTION OF REFERENCE NUMERALS AND SIGNS 101 modified ferritin Fer8-98glu
102 modification position (position 91 of glutamic acid)
201 Fer8-98glu solution after introduction of iron oxide core
202 supernatant liquid of Fer8-98glu
203 precipitate of Fer8-98glu
204 Fer8-159glu solution after introduction of iron oxide core
205 supernatant liquid of Fer8-159glu
206 precipitate of Fer8-159glu
301 silicon substrate
302 silicon oxide film
303a electron beam resist film
303b electron beam resist spot
304 molecular film spot
305 substrate having molecular film spot
306 ferritin
306a ferritin in solution
306b ferritin on molecular film spot
307 ferritin solution
308 substrate including ferritin arranged on molecular film

---

What is claimed is:

1. A method of arranging ferritin on a substrate with a plurality of molecular film spots, comprising:
   preparing a modified ferritin consisting of twenty-four protein subunits, wherein each of the twenty-four protein subunits consists of the amino acid sequence set out in SEQ ID NO: 1; and
   arranging one molecule of the modified ferritin on each of a plurality of molecular film spots by bringing a solution containing the modified ferritin into contact with the substrate with the plurality of molecular film spots, wherein,
   each molecular film spot has an amino group on the surface thereof; and
   the area of one molecular film spot is equal to or less than 2,100 nm$^2$.

2. The method according to claim 1 wherein the modified ferritin includes an iron oxide particle therein.

3. The method according to claim 1 wherein the molecular film spot comprises an aminosilane molecular film.

4. The method according to claim 1 wherein the substrate is a silicon substrate with a silicon oxide film present on its surface except at regions where the molecular film spot is present on the silicon substrate surface.

5. The method according to claim 1 wherein the area of one molecular film spot is equal to or greater than 380 nm$^2$.

6. The method according to claim 1, further comprising prior to the arrangement step, a molecular film spot formation step of forming the molecular film spot by photolithography.

7. A method of arranging inorganic particles on a substrate, the method comprising:
   an arrangement step of arranging one molecule of ferritin on each of a plurality of molecular film spots by bringing a solution containing the ferritin into contact with the substrate with the plurality of molecular film spots; and
   a decomposition step of decomposing the ferritin by heating the substrate, wherein the ferritin is modified ferritin consisting of twenty-four protein subunits, and each of the twenty-four protein subunits consists of the amino acid sequence set out in SEQ ID NO: 1;
   the molecular film spots have an amino group on the surface thereof; and
   the area of one molecular film spot is equal to or less than 2,100 nm$^2$.

8. The method according to claim 7 wherein the modified ferritin includes an iron oxide particle therein.

9. The method according to claim 7 wherein each molecular film spot comprises an aminosilane molecular film.

10. The method according to claim 7 wherein the substrate is a silicon substrate, with a silicon oxide film present on its surface except at regions where the molecular film spot is present on the silicon substrate surface.

11. The method according to claim 7 wherein the area of one molecular film spot is equal to or greater than 380 nm$^2$.

12. The method according to claim 7, further comprising prior to the arrangement step, a molecular film spot formation step of forming the molecular film spot by photolithography.

* * * * *

SEQUENCE LISTING

<160> NUMBER OF SEQ ID NOS: 6

<210> SEQ ID NO 1
<211> LENGTH: 168
<212> TYPE: PRT
<213> ORGANISM: Artificial Sequence
<220> FEATURE:
<223> OTHER INFORMATION: A modified horse ferritin (apoFer8-98glu)

<400> SEQUENCE: 1

```
Met Tyr Ser Thr Glu Val Glu Ala Ala Val Asn Arg Leu Val Asn Leu
1               5                   10                  15

Tyr Leu Arg Ala Ser Tyr Thr Tyr Leu Ser Leu Gly Phe Tyr Phe Asp
            20                  25                  30

Arg Asp Asp Val Ala Leu Glu Gly Val Cys His Phe Phe Arg Glu Leu
        35                  40                  45

Ala Glu Glu Lys Arg Glu Gly Ala Glu Arg Leu Leu Lys Met Gln Asn
    50                  55                  60

Gln Arg Gly Gly Arg Ala Leu Phe Gln Asp Leu Gln Lys Pro Ser Gln
65                  70                  75                  80

Asp Glu Trp Gly Thr Thr Pro Asp Ala Met Glu Ala Ala Ile Val Leu
                85                  90                  95

Glu Lys Ser Leu Asn Gln Ala Leu Leu Asp Leu His Ala Leu Gly Ser
            100                 105                 110

Ala Gln Ala Asp Pro His Leu Cys Asp Phe Leu Glu Ser His Phe Leu
        115                 120                 125

Asp Glu Glu Val Lys Leu Ile Lys Lys Met Gly Asp His Leu Thr Asn
    130                 135                 140

Ile Gln Arg Leu Val Gly Ser Gln Ala Gly Leu Gly Glu Tyr Leu Phe
145                 150                 155                 160

Glu Arg Leu Thr Leu Lys His Asp
                165
```

<210> SEQ ID NO 2
<211> LENGTH: 507
<212> TYPE: DNA
<213> ORGANISM: Artificial Sequence
<220> FEATURE:
<223> OTHER INFORMATION: A modified DNA of horse ferritin
      (apoFer8-98glu)

<400> SEQUENCE: 2

```
atgtattcta ctgaagtgga ggccgccgtc aaccgcctgg tcaacctgta cctgcgggcc      60
tcctacacct acctctctct gggcttctat ttcgaccgcg acgatgtggc tctggagggc     120
gtatgccact tcttccgcga gttggcggag gagaagcgcg agggtgccga gcgtctcttg     180
```

```
aagatgcaaa accagcgcgg cggccgcgct ctcttccagg acttgcagaa gccgtcccag    240
gatgaatggg gtacaacccc agacgccatg gaagccgcca ttgtcctgga gaagagcctg    300
aaccaggccc ttttggatct gcatgccctg ggttctgccc aggcagaccc ccatctctgt    360
gacttcttgg agagccactt cctagacgag gaggtgaaac tcatcaagaa gatgggcgac    420
catctgacca acatccagag gctcgttggc tcccaagctg ggctgggcga gtatctcttt    480
gaaaggctca ctctcaagca cgactaa                                        507
```

<210> SEQ ID NO 3
<211> LENGTH: 168
<212> TYPE: PRT
<213> ORGANISM: Artificial Sequence
<220> FEATURE:
<223> OTHER INFORMATION: A modified horse ferritin (apoFer8)

<400> SEQUENCE: 3

```
Met Tyr Ser Thr Glu Val Glu Ala Ala Val Asn Arg Leu Val Asn Leu
1               5                   10                  15

Tyr Leu Arg Ala Ser Tyr Thr Tyr Leu Ser Leu Gly Phe Tyr Phe Asp
            20                  25                  30

Arg Asp Val Ala Leu Glu Gly Val Cys His Phe Phe Arg Glu Leu
        35                  40                  45

Ala Glu Glu Lys Arg Glu Gly Ala Glu Arg Leu Leu Lys Met Gln Asn
    50                  55                  60

Gln Arg Gly Gly Arg Ala Leu Phe Gln Asp Leu Gln Lys Pro Ser Gln
65                  70                  75                  80

Asp Glu Trp Gly Thr Thr Pro Asp Ala Met Lys Ala Ala Ile Val Leu
                85                  90                  95

Glu Lys Ser Leu Asn Gln Ala Leu Leu Asp Leu His Ala Leu Gly Ser
            100                 105                 110

Ala Gln Ala Asp Pro His Leu Cys Asp Phe Leu Glu Ser His Phe Leu
        115                 120                 125

Asp Glu Glu Val Lys Leu Ile Lys Lys Met Gly Asp His Leu Thr Asn
    130                 135                 140

Ile Gln Arg Leu Val Gly Ser Gln Ala Gly Leu Gly Glu Tyr Leu Phe
145                 150                 155                 160

Glu Arg Leu Thr Leu Lys His Asp
                165
```

<210> SEQ ID NO 4
<211> LENGTH: 168
<212> TYPE: PRT
<213> ORGANISM: Artificial Sequence
<220> FEATURE:
<223> OTHER INFORMATION: A modified horse ferritin (apoFer8-159glu)

<400> SEQUENCE: 4

```
Met Tyr Ser Thr Glu Val Glu Ala Ala Val Asn Arg Leu Val Asn Leu
1               5                   10                  15

Tyr Leu Arg Ala Ser Tyr Thr Tyr Leu Ser Leu Gly Phe Tyr Phe Asp
            20                  25                  30

Arg Asp Val Ala Leu Glu Gly Val Cys His Phe Phe Arg Glu Leu
        35                  40                  45

Ala Glu Glu Lys Arg Glu Gly Ala Glu Arg Leu Leu Lys Met Gln Asn
    50                  55                  60

Gln Arg Gly Gly Arg Ala Leu Phe Gln Asp Leu Gln Lys Pro Ser Gln
65                  70                  75                  80
```

-continued

```
Asp Glu Trp Gly Thr Thr Pro Asp Ala Met Lys Ala Ala Ile Val Leu
            85                  90                  95

Glu Lys Ser Leu Asn Gln Ala Leu Leu Asp Leu His Ala Leu Gly Ser
        100                 105                 110

Ala Gln Ala Asp Pro His Leu Cys Asp Phe Leu Glu Ser His Phe Leu
        115                 120                 125

Asp Glu Glu Val Lys Leu Ile Lys Lys Met Gly Asp His Leu Thr Asn
    130                 135                 140

Ile Gln Arg Leu Val Gly Ser Glu Ala Gly Leu Gly Glu Tyr Leu Phe
145                 150                 155                 160

Glu Arg Leu Thr Leu Lys His Asp
                165
```

<210> SEQ ID NO 5
<211> LENGTH: 168
<212> TYPE: PRT
<213> ORGANISM: Artificial Sequence
<220> FEATURE:
<223> OTHER INFORMATION: A modified horse ferritin (apoFer8-157glu)

<400> SEQUENCE: 5

```
Met Tyr Ser Thr Glu Val Glu Ala Ala Val Asn Arg Leu Val Asn Leu
1               5                   10                  15

Tyr Leu Arg Ala Ser Tyr Thr Tyr Leu Ser Leu Gly Phe Tyr Phe Asp
            20                  25                  30

Arg Asp Asp Val Ala Leu Glu Gly Val Cys His Phe Phe Arg Glu Leu
        35                  40                  45

Ala Glu Glu Lys Arg Glu Gly Ala Glu Arg Leu Leu Lys Met Gln Asn
    50                  55                  60

Gln Arg Gly Gly Arg Ala Leu Phe Gln Asp Leu Gln Lys Pro Ser Gln
65                  70                  75                  80

Asp Glu Trp Gly Thr Thr Pro Asp Ala Met Lys Ala Ala Ile Val Leu
            85                  90                  95

Glu Lys Ser Leu Asn Gln Ala Leu Leu Asp Leu His Ala Leu Gly Ser
        100                 105                 110

Ala Gln Ala Asp Pro His Leu Cys Asp Phe Leu Glu Ser His Phe Leu
        115                 120                 125

Asp Glu Glu Val Lys Leu Ile Lys Lys Met Gly Asp His Leu Thr Asn
    130                 135                 140

Ile Gln Arg Leu Val Glu Ser Gln Ala Gly Leu Gly Glu Tyr Leu Phe
145                 150                 155                 160

Glu Arg Leu Thr Leu Lys His Asp
                165
```

<210> SEQ ID NO 6
<211> LENGTH: 168
<212> TYPE: PRT
<213> ORGANISM: Artificial Sequence
<220> FEATURE:
<223> OTHER INFORMATION: A modified horse ferritin
      (apoFer8-98glu105glu)

<400> SEQUENCE: 6

```
Met Tyr Ser Thr Glu Val Glu Ala Ala Val Asn Arg Leu Val Asn Leu
1               5                   10                  15

Tyr Leu Arg Ala Ser Tyr Thr Tyr Leu Ser Leu Gly Phe Tyr Phe Asp
            20                  25                  30

Arg Asp Asp Val Ala Leu Glu Gly Val Cys His Phe Phe Arg Glu Leu
        35                  40                  45
```

-continued

```
Ala Glu Glu Lys Arg Glu Gly Ala Glu Arg Leu Leu Lys Met Gln Asn
     50                  55                  60

Gln Arg Gly Gly Arg Ala Leu Phe Gln Asp Leu Gln Lys Pro Ser Gln
65                   70                  75                  80

Asp Glu Trp Gly Thr Thr Pro Asp Ala Met Glu Ala Ala Ile Val Leu
                 85                  90                  95

Glu Glu Ser Leu Asn Gln Ala Leu Leu Asp Leu His Ala Leu Gly Ser
             100                 105                 110

Ala Gln Ala Asp Pro His Leu Cys Asp Phe Leu Glu Ser His Phe Leu
         115                 120                 125

Asp Glu Glu Val Lys Leu Ile Lys Lys Met Gly Asp His Leu Thr Asn
     130                 135                 140

Ile Gln Arg Leu Val Gly Ser Gln Ala Gly Leu Gly Glu Tyr Leu Phe
145                 150                 155                 160

Glu Arg Leu Thr Leu Lys His Asp
                 165
```